(12) United States Patent
Nam et al.

(10) Patent No.: US 8,557,559 B2
(45) Date of Patent: Oct. 15, 2013

(54) SELF-DYING RECOMBINANT MICROORGANISM FOR MEASURING SOIL AND WATER CONTAMINATION

(75) Inventors: Kyoung Phile Nam, Seoul (KR); Doyun Shin, Seoul (KR)

(73) Assignee: SNU R&DB Foundation, Seoul (KR)

( * ) Notice: Subject to any disclaimer, the term of this patent is extended or adjusted under 35 U.S.C. 154(b) by 314 days.

(21) Appl. No.: 13/034,198

(22) Filed: Feb. 24, 2011

(65) Prior Publication Data

US 2012/0135502 A1    May 31, 2012

(30) Foreign Application Priority Data

Nov. 26, 2010    (KR) .......................... 10-2010-0118540

(51) Int. Cl.
*C12S 1/00*    (2006.01)

(52) U.S. Cl.
USPC .................................... 435/252.3; 435/262.5

(58) Field of Classification Search
USPC ...................................................... 435/252.1
See application file for complete search history.

(56) References Cited

PUBLICATIONS

Palmer, et al., Use of Lux-Based Biosensors for Rapid Diagnosis of Pollutants in Arable Soils, Chemosphere, vol. 36, No. 12, pp. 2683-2697, 1998 Elsevier Science Ltd., Great Britain.
Sousa, et al., Use of a Lux-Modified Bacterial Biosensor to Identify Constraints to Bioremediation of BTEX-Contaminated Sites, Environmental Toxicology and Chemistry, vol. 17, No. 6, pp. 1039-1045, 1998 SETAC, USA.
Weissenfels, et al., Adsorption of Polycyclic Aromatic Hydrocarbons (PAHs) by Soil Particles; Influence on Biodegradability and Biotoxicity, Applied Microbiology Biotechnology, 36:689-696, 1992 Springer-Verlag, Federal Republic of Germany.
Tang, et al., Mild Extractability and Bioavailability of Polycyclic Aromatic Hydrocarbons in Soil, Environmental Toxicology and Chemistry, vol. 18, No. 12, pp. 2711-2714, 1999 SETAC, USA.
Alexander, et al., Bioavailability of Genotoxic Compounds in Soils, Environmental Science & Technology, vol. 34, No. 8, pp. 1589-1593, 2000, USA.
Reid, et al., Nonexhaustive Cyclodextrin-Based Extraction Technique for the Evaluation of PAH Bioavailability, Environmental Science & Technology, vol. 34, No. 15, pp. 3174-3179, 2000 USA.
King, et al., Rapid, Sensitive Bioluminescent Reporter Technology for Naphthalene Exposure and Biodegradation, Science, vol. 249, pp. 778-781, Aug. 17, 1990, USA.
Willardson, et al., Development and Testing of a Bacterial Biosensor for Toluene-Based Environmental Contaminants, Applied and Environmental Microbiology, vol. 64, No. 3, pp. 1006-1012, 1998 American Society for Microbiology, USA.
Gu, et al., Soil Biosensor for the Detection of PAH Toxicity Using an Immobilized Recombinant Bacterium and a Biosurfactant, Biosensors & Bioelectronics, vol. 16, pp. 667-674, 2001 Elsevier, South Korea.
Shin, Doyun, "Microbial Visualization System to Identify the Relative Location and Toxicity of Phenanthrene," Department of Civil and Environmental Engineering, Seoul National University, Aug. 2010 (60 pgs.).

*Primary Examiner* — Tekchand Saidha
*Assistant Examiner* — Rama P Ramanujam
(74) *Attorney, Agent, or Firm* — Patterson Thuente Pedersen, P.A.

(57) ABSTRACT

Provided is *Sphingomonas paucimobilis* (SEQ ID NO. 1) having base sequences of which a sequence number is 1, being deposited with a deposition number KCTC 11771BP, and being used for specifically measuring aromatic hydrocarbons as a contaminant in a sample.

4 Claims, 8 Drawing Sheets
(2 of 8 Drawing Sheet(s) Filed in Color)

| | Phenanthrene concentration in sand-water mixture (mg/kg-sand) | | | | | |
|---|---|---|---|---|---|---|
| | 0 | 50 | 150 | 250 | 500 | 1000 |
| Strain S | (1.00) | (0.83±0.06) | (0.73±0.06) | (0.71±0.04) | (0.55±0.10) | (0.40±0.07) |

| Conc. of phenanthrene in soil-water mixture (mg/kg-soil) | | | | | |
|---|---|---|---|---|---|
| 0 | 50 | 150 | 250 | 500 | 1000 |
|  |  |  |  |  |  |
| (1.00) | (1.01±0.08) | (0.87±0.14) | (0.69±0.14) | (0.66±0.10) | (0.69±0.14) |

```
                        SEQUENCE LISTING

<160> NUMBER OF SEQ ID NOS: 1

<210> SEQ ID NO 1
<211> LENGTH: 500
<212> TYPE: DNA
<213> ORGANISM: Artificial Sequence
<220> FEATURE:
<223> OTHER INFORMATION: SEQ ID NO. 1 - A recombinant strain of
      Sphingomonas paucimobilis

<400> SEQUENCE: 1
ccaattcccc aatgagcggc agccggttcg gaccgcttcc cggtgaatga ctggaattcc      60
ttggcggtgt tccggaatcc gtccccgagc cgcccgccca tgacgggcga atcgatgaat     120
agacatttat gttgcgctat tcctacacca acaaattacc cggtgcaacg tattgcagta    180
tggagaacta tcgcatagac tcggccggca agaccggcgg caagacaatc ggcgatgacg    240
gtcccgcgag atgcgagccg cgtcctctgg gagagaaagc aaatggcagc agtcacggaa    300
ctcggttacc tggtcaagga gaagagagca atgaagcagc ataaggcgat gattgtcgcc    360
ctgatcgtca tctgtatcac cgccgtagtg gcggcgctgg taacgagaaa agacctctgt    420
gaggttcaca tccgaactgg ccagacggag gttgctgttt tcacggctta cgaatccgag    480
taagagcaac ggcggggagt                                                500
```

SELF-DYING RECOMBINANT MICROORGANISM FOR MEASURING SOIL AND WATER CONTAMINATION

CROSS-REFERENCE TO RELATED APPLICATION

This application claims the benefit of Korean Patent Application No. 10-2010-0118540, filed on Nov. 26, 2010, in the Korean Intellectual Property Office, the disclosure of which is incorporated herein by reference.

A Sequence Listing appended to the present specification is herein incorporated by reference in its entirety.

BACKGROUND

1. Field of the Invention

The present invention relates to a self-dying recombinant strain for measuring contamination of soil or water.

2. Description of the Related Art

A concentration of a contaminant in soil or ground water, a bioavailable concentration, and a concentration of toxicity are different from each other, since a toxicity and a bioavailability of the contaminant is reduced by a process, such as, sorption and the like, performed after the contaminant is released into soil. Therefore, when a toxicity with respect to a receptor is measured, analyzing a toxicity and a bioavailability of a target contaminant may be significantly important.

Various schemes for measuring the toxicity and the bioavailability of the contaminant in soil or groundwater have been developed. Microtox is a toxicity measuring scheme that measures the toxicity of the contaminant based on a degree of inhibition of luminance of a bioluminescent microorganism (Palmer et al., 1998; Sousa et al., 1998). In addition, measuring a biodegradability (Weissenfels et al., 1992; Tang and Alexander, 1999) or a mild extraction (Alexander and Alexander, 2000; Reid et al., 2000) have been widely used. The above mentioned schemes have drawbacks. For example, the schemes may not be compound-specific, the schemes may need to be compared with an organism-based detection scheme, or the schemes may not directly measure the contaminant when the contaminant is in soil. Therefore, the schemes may not take account of interaction between organisms existing in soil or water and the contaminant.

A contaminant detection scheme using a recombinant microorganism has drawn attention since G. Sayler suggested the scheme in the early 1990s. A microorganism is used as a device for specifically and sensitively detecting the contaminant. In most cases, the contaminant detection scheme may be based on a scheme of measuring an amount of luminescence or fluorescence. A promoter of a gene expressed by a target contaminant is combined with a luminescent or fluorescent gene and thus, as an amount of contaminant increases, an amount of luminescence or fluorescence also increases.

When the contaminant contained in soil or water is measured using a recombinant microorganism, the contaminant is extracted from soil, the extracted contaminant is reacted with a recombinant strain, and the reaction is measured. According to the study of Willardson et al. in 1998, BTEX concentrations in soil were measured using a bioreporter *Pseudomonas putida* mt-2, and a reaction of the bioreporter is measured using soil-ethanol extract to remove the disturbance of soil particles. According to the study of Gu and Chang in 2001, all phenanthrene is extracted using a surfactant, and a toxicity of phenanthrene in soil is measured. However, the above mentioned studies include an extracting process and thus, may not appropriately show the bioavailability and the toxicity of the contaminant.

SUMMARY

An aspect of the present invention provides a novel strain that may detect, as an indicator of contamination, aromatic hydrocarbons existing in soil contaminated by oil or existing in oil in water and thus, may measure soil or water contamination and may predict a residual toxicity and a bioavailability of oil contaminated soil or water.

According to an aspect of the present invention, there is provided *Sphingomonas paucimobilis* SEQ ID NO. 1 having base sequences of which a sequence number is 1, being deposited at the Korea Research Institute of Bioscience and Biotechnology (KRIBB), located at 111 Gwanhongno, Yuseong-gu, Daejeon 305-806, Republic of Korea, with a deposition number KCTC 11771BP (deposited Oct. 1, 2010), and being used for specifically measuring aromatic hydrocarbons as a contaminant in a sample.

Additional aspects, features, and/or advantages of the invention will be set forth in part in the description which follows and, in part, will be apparent from the description, or may be learned by practice of the invention.

EFFECT

According to the present invention, a self-dying recombinant strain may quantitatively visualize a toxicity and a bioavailability of aromatic hydrocarbons, as an index of contaminant. The recombinant strain shows a death reaction based on an amount of an available aromatic hydrocarbon and thus, a dyeing scheme shows that an amount of fluorescence of microorganisms may be reduced when the amount of an available aromatic hydrocarbon decreases.

As a concentration of the available aromatic hydrocarbon is higher, a number of dead novel recombinant microorganisms increases, as opposed to a conventional fluorescence-emitting recombinant microorganism for detecting a contaminant. Accordingly, when the residual toxicity of the aromatic hydrocarbon is visualized, soil or water contamination may be measurable. A technology for constructing the plasmid for the novel recombinant microorganism is different from a conventional technology. The self-dying recombinant microorganism may be *shown* dead by a portion indicating a toxicity of the aromatic hydrocarbon existing in soil and water.

A fluorescence reaction of a conventional fluorescence-emitting recombinant strain with respect to a contaminant existing in soil may be difficult to be measured and thus, the contaminant is extracted from soil to measure the reaction. According to the present invention, after a sample soil and a recombinant strain are mixed, a toxicity and a bioavailability of a contaminant may be measured without an extracting process. Also, a microorganism is used as a detecting device and thus, a toxicity that affects organisms may be measured.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects, features, and advantages of the invention will become apparent and more readily appreciated from the following description of embodiments, taken in conjunction with the accompanying drawings of which.

DETAILED DESCRIPTION

Reference will now be made in detail to embodiments of the present invention, examples of which are illustrated in the accompanying drawings, wherein like reference numerals refer to the like elements throughout. Embodiments are described below to explain the present invention by referring to the figures.

Example embodiments may provide *Sphingomonas paucimobilis* SEQ ID NO. 1 having base sequences of which a sequence number is 1, being deposited with a deposition number KCTC 11771BP (deposited Oct. 1, 2010), and specifically measuring aromatic hydrocarbons as a contaminant in a sample. An index of the contaminant, which is measured by the strain, may be the aromatic hydrocarbon, particularly, phenanthrene. The aromatic hydrocarbon may be a component having a high residual toxicity among components of oil when soil or water is contaminated by oil. Phenanthrene may be a representative of polycyclic aromatic hydrocarbons (PAHs) among aromatic hydrocarbons.

*Sphingomonas paucimobilis* (SEQ ID NO. 1) and the sample may be mixed, the mixture may be stained using the LIVE/DEAD BacLight bacterial viability kit (molecular probes, L7012) of INVITROGEN, and a fluorescence reaction may be measured by a micro-plate reader. The LIVE/DEAD BacLight bacterial viability kit may label, using a DNA-binding dye, DNA of a live microorganism with green fluorescence and may label, using the DNA-binding dye, DNA of a dead microorganism with red fluorescence. Therefore, as an amount of red fluorescence increases, a degree of contamination of the sample also increases. Microorganisms may die on the initiation of phenanthrene biodegradation and thus, may be labeled as dead microorganisms. The contaminant included in the mixture may be quantified based on an image analysis.

A confocal laser scanning microscope (CLSM) may measure a fluorescence reaction of the mixture of a soil sample and microorganisms to analyze phenanthrene in the soil sample. An image including measured green fluorescence and measured red fluorescence may be converted into a grayscale image after removing the measured red fluorescence from the image based on Adobe Photoshop CS4 (Adobe Systems, CA, USA). An integrated fluorescence intensity in an image of 254×254 pixels was quantified using a measure function of ImageJ program (ImageJ; Rasband, 1997-2009). The integrated fluorescence intensity may be a value obtained by dividing sum of illuminance of all the pixels by a number of the pixels in the image.

EXAMPLE

Example 1

Construction of Recombinant Strain

A recombinant strain, *Sphingomonas paucimobilis* (SEQ ID NO. 1), was constructed using *Sphingomonas paucimobilis* EPA505 that is a microorganism degrading aromatic hydrocarbons.

pBBR1-MCS2 that is a broad-host range vector was used as a vector for construction of the recombinant strain. A recombinant plasmid was obtained by recombining a promoter site of pbhA gene that is expressed by aromatic hydrocarbons and gef gene that is a microorganism-killing gene, using pBBR1-MCS2. *Sphingomonas paucimobilis* SQL2 was constructed by inserting the recombinant plasmid to *Sphingomonas paucimobilis* EPA505.

Figure 1:
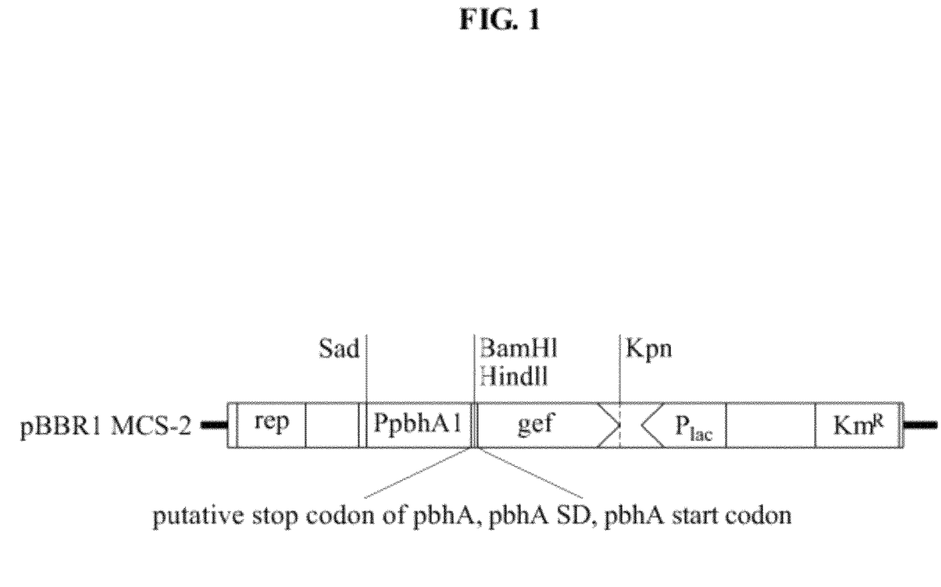
FIG. 1 is a diagram illustrating a structure of a recombinant gene fragment according to an embodiment of the present invention.

FIG. 1 illustrates a structure of a recombinant gene fragment according to an embodiment of the present invention.

Referring to FIG. 1, PpbhA1 may denote a putative promoter region of pbhA gene, $Km^R$ may denote a kanamycin-resistance gene, gef may denote a microorganism-killing gene (gene expression fatal), and rep may denote an origin of replication.

The recombinant strain, *Sphingomonas paucimobilis* (SEQ ID NO. 1), may be designed to express gef gene that kills the microorganism when pbhA gene is expressed by available phenanthrene.

Example 2

Verification of Substrate Specificity

Phenanthrene was added to an inorganic medium including pyruvate as a carbon source, up to phenanthrene concentrations of about 50 mg/L through about 500 mg/L, the recombinant strain was inoculated, and a sample was taken every 24-hour and stained using LIVE/DEAD BacLight bacterial viability kit (Molecular Probes, L7012) and a fluorescence reaction was measured by a micro-plate reader.

A reaction of the recombinant strain with respect to an inorganic medium including hexane and hexadecane that are aliphatic hydrocarbon having the equivalent concentration, hexane concentrations being about 50 mg/L through about 500 mg/L and hexadecane concentrations being about 50 mg/L through about 500 mg/L, and a reaction of the recombinant strain with respect to an inorganic medium including toluene that is a monoaromatic hydrocarbon, toluene concentrations being about 1 mg/L through about 50 mg/L, were respectively measured for comparison.

The aliphatic hydrocarbon which is a component of oil, along with aromatic hydrocarbons, was selected to show that the recombinant strain selectively detects aromatic hydrocarbons included in oil. The LIVE/DEAD BacLight bacterial viability kit is a dying scheme that labels, using a DNA-binding dye, DNA of a live microorganism with green fluorescence and labels, using the DNA-binding dye, DNA of dead microorganism with red fluorescence and thus, indicates a viability of microorganisms.

The reaction of the recombinant strain was expressed by a relative fluorescence intensity $FL/FL_0$, that is, a value obtained by dividing a fluorescence reaction value FL of a recombinant strain exposed to a target contaminant by a fluorescence reaction value $FL_0$ of a recombinant strain that is not exposed to the target contaminant. The relative fluorescence intensity $FL/FL_0$ expresses the reaction of the recombinant strain, which is based on a concentration of contaminant, with a rate of decreasing fluorescence and thus, an error rate may be reduced during a test, and a concentration of toxicity may be expressed with a standardized fluorescence intensity value.

Figure 2:
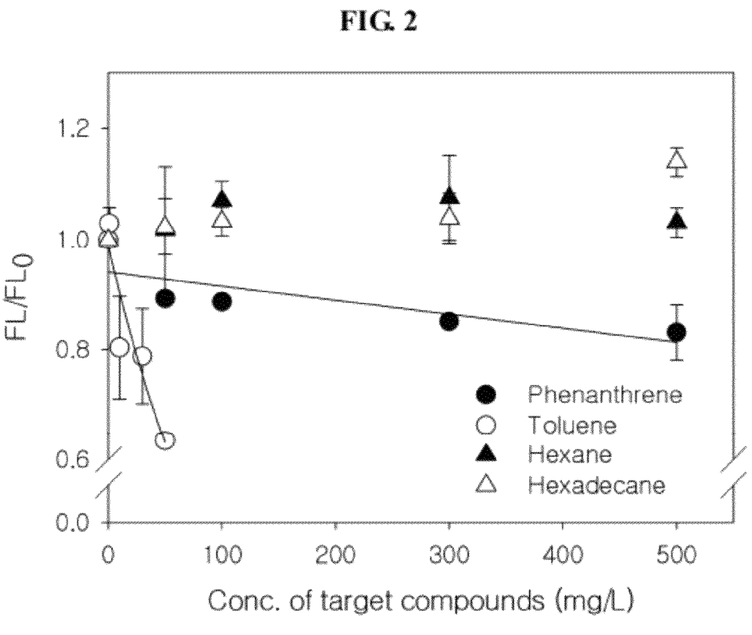
FIG. 2 is a graph illustrating a reaction of a recombinant strain with respect to phenanthrene, toluene, hexane, and hexadecane.

FIG. 2 illustrates a response of a recombinant strain with respect to phenanthrene, toluene, hexane, and hexadecane.

Referring to FIG. 2, the recombinant strain may not respond with hexane and hexadecane that are aliphatic hydrocarbon, and may show a death response with respect to phenanthrene that is aromatic hydrocarbons and thus, may show that a fluorescence response is specifically decreased. The reaction may be quantitatively and linearly performed with respect to a concentration of phenanthrene. In a case of toluene, a reaction with respect to toluene is measured in a low toluene concentration, that is, toluene concentrations of about 1 mg/L through 50 mg/L, since a high toluene concentration may be toxic to a microorganism.

Therefore, it is verified that the recombinant strain specifically detects a toxicity and a bioavailability of aromatic hydrocarbons included in oil.

Example 3

Verification of Performance of Recombinant Strain in Model Soil

Ottawa sand was used as a model soil. The model soil was contaminated with phenanthrene up to concentrations from 50 mg/kg to 1000 mg/kg, an inorganic medium including pyruvate as a source of carbon was added, the inorganic medium of 10 mL per the model soil of 2 g, the recombinant strain was inoculated, and a sample was taken every 24-hour to measure a fluorescence response.

A fluorescence response was photographed by a CLSM to directly measure a mixture of the model soil, the liquid medium, and the recombinant strain, and the measured fluorescence reaction was quantified using an ImageJ program. Table 1 compares characteristics of the model soil and characteristics of a real soil (M soil).

TABLE 1

| | Soil texture | Organic matter content in soil (%) | Field moisture capacity | Hydrogen ion concentration (pH) | Area $(m^2/g)^a$ |
|---|---|---|---|---|---|
| Ottawa sand | Sand | 0 | 0.050 | 7.0 | 0.13 |
| M soil | Sandy loam | 11.5 | 0.358 | 6.8 | 2.4 |

Figure 3:
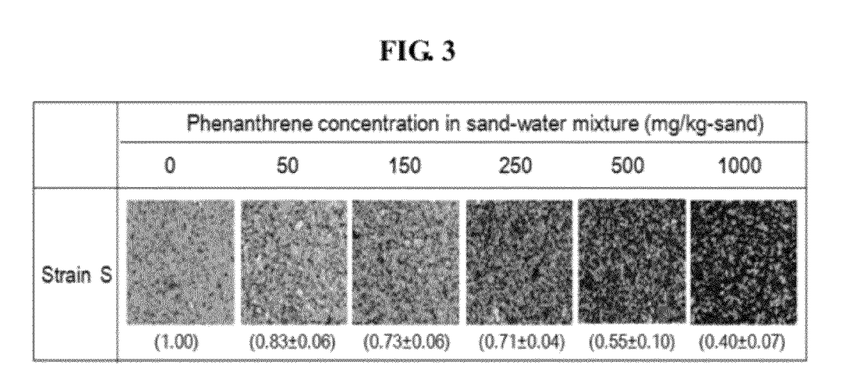
FIG. 3 is a picture, photographed by a confocal laser scanning microscope (CLSM), of a reaction of a recombinant strain with respect to phenanthrene contaminated Ottawa sand.

FIG. 3 is a picture, photographed by a CLSM, of a response of a recombinant strain with respect to phenanthrene contaminating Ottawa sand. In this example, a magnification may be 200, and a value in parentheses may denote a relative fluorescence intensity ($FL/FL_0$) with a standard deviation.

Referring to FIG. 3, as phenanthrene concentrations increase, a number of live microorganisms decrease. Therefore, it is verified that the recombinant strain successfully detects phenanthrene in Ottawa sand. As phenanthrene concentrations become higher, a number of dead microorganisms become higher and thus, the recombinant strain represents a toxicity of phenanthrene. Therefore, the relative fluorescence intensity ($FL/FL_0$) of the recombinant strain may represent a concentration of toxicity of phenanthrene.

Figure 4:
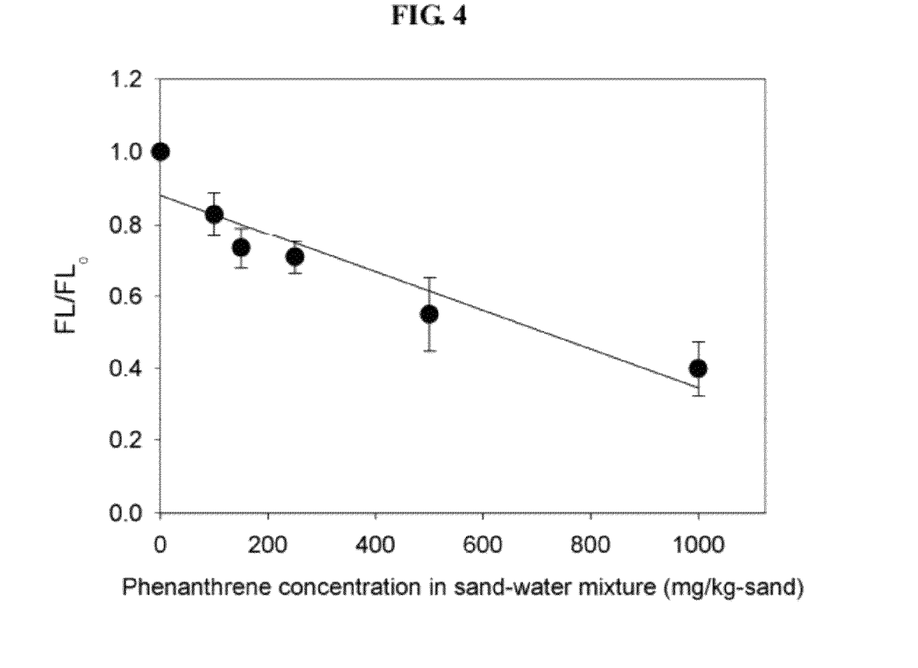
FIG. 4 is a graph quantitatively illustrating a reaction of a recombinant strain with respect to phenanthrene concentrations in Ottawa sand.

FIG. 4 is a graph quantitatively illustrating a reaction of a recombinant strain with respect to phenanthrene concentrations in Ottawa sand.

Referring to FIG. 4, as phenanthrene concentrations becomes higher, a reaction of the recombinant strain becomes lower, and the reaction may be quantitatively and linearly performed with respect to the concentration.

Example 4

Verification of Performance of Recombinant Strain in Real Soil

Phenanthrene was added to soil that had not been contaminated with phenanthrene up to concentrations from 50 mg/kg to 1000 mg/kg, an inorganic medium was added, the inorganic medium of 10 mL per soil of 2 g, the recombinant strain was inoculated and cultivated for 24-hours, and a reaction was measured in the same manner as Example 3.

Figure 5:
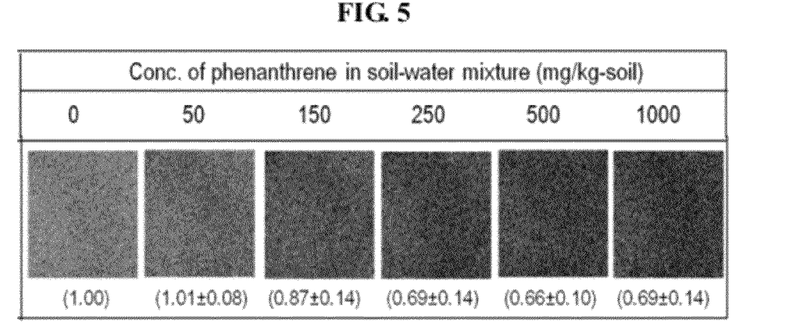
FIG. 5 is a picture, photographed by a CLSM, of a reaction of a recombinant strain with respect to phenanthrene contaminating a real soil.

FIG. 5 is a picture, photographed by a CLSM, of a reaction of a recombinant strain with respect to phenanthrene contaminating a real soil. In this example, a magnification may be 200, and a value in parentheses may denote a relative fluorescence intensity ($FL/FL_0$) with a standard deviation.

Figure 6:
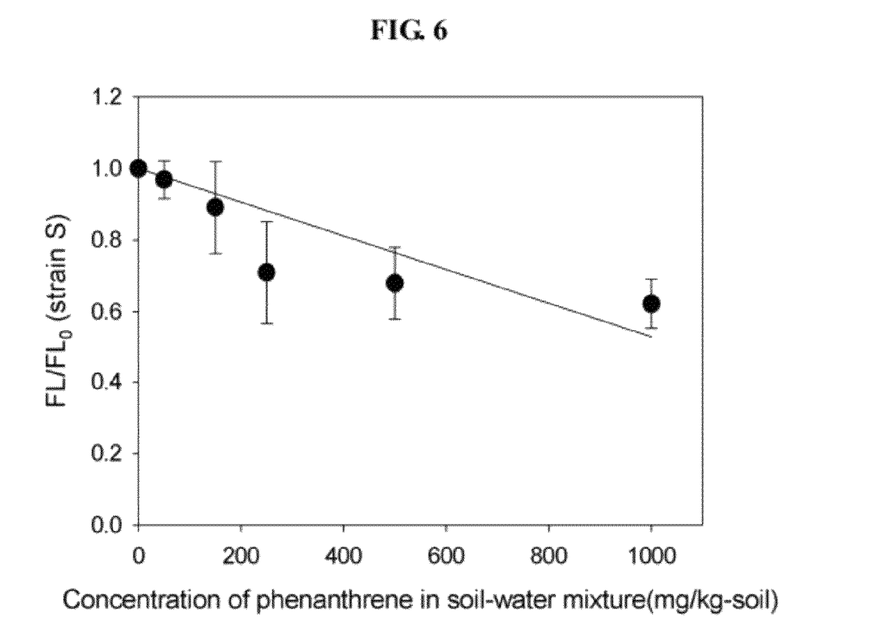
FIG. 6 is a graph quantitatively illustrating a reaction of a recombinant strain with respect to phenanthrene concentrations in a real soil.

FIG. 6 is a graph quantitatively illustrating a reaction of a recombinant strain with respect to phenanthrene concentrations in a real soil.

Referring to FIGS. 5 and 6, the reaction of the recombinant strain may be quantitatively and linearly performed in the same manner as in the Ottawa sand, and the reaction may be significantly sensitive to phenanthrene concentrations.

Conventional contaminant detecting methods using a fluorescence-emitting microorganism may show great performance in a model soil, such as Ottawa sand and the like, but have difficulty in detecting a contaminant in a real soil. Conversely, according to the present invention, a reaction of the recombinant strain with respect to phenanthrene may be measured in the real soil without difficulty. Conventional fluorescence-emitting recombinant microorganism strains are able to measure only phenanthrene of at least about 1,000 mg/kg, whereas the recombinant strain of the present invention is able to measure from phenanthrene of about 50 mg/kg.

Example 5

Comparison of Biodegradation of Phenanthrene in Model Soil and Real Soil Using a Recombinant Strain Phenanthrene was added to each of the model soil and the real soil up to phenanthrene concentrations of about 500 mg/kg, an inorganic medium was added, the inorganic medium of 10 mL per soil of 2 g, the recombinant strain was inoculated, and an amount of residual phenanthrene was extracted and measured every 24-hour. Extraction of phenanthrene was performed based on the Environmental Protection Agency (EPA) method 3545 to extract all extractable phenanthrene in soil.

An applicability of the recombinant strain in the real soil and an applicability of the recombinant strain in the model soil was compared and analyzed to measure a residual toxicity and a bioavailability of oil contaminating the real soil.

The reaction of the recombinant strain is controlled by a promoter of pbhA gene. The pbhA gene is associated with a first operation of biodegradation of phenanthrene and thus, pbhA gene may express to be proportional to an amount of phenanthrene degraded by the recombinant strain. Accordingly, when an amount of degraded phenanthrene is measured under a given condition, a response of the recombinant strain with respect to phenanthrene may be predicted. When the reaction is different from the predicted amount of biodegradation, it is determined that a performance of the recombinant strain for detecting phenanthrene is reduced by an external condition.

Figure 7:
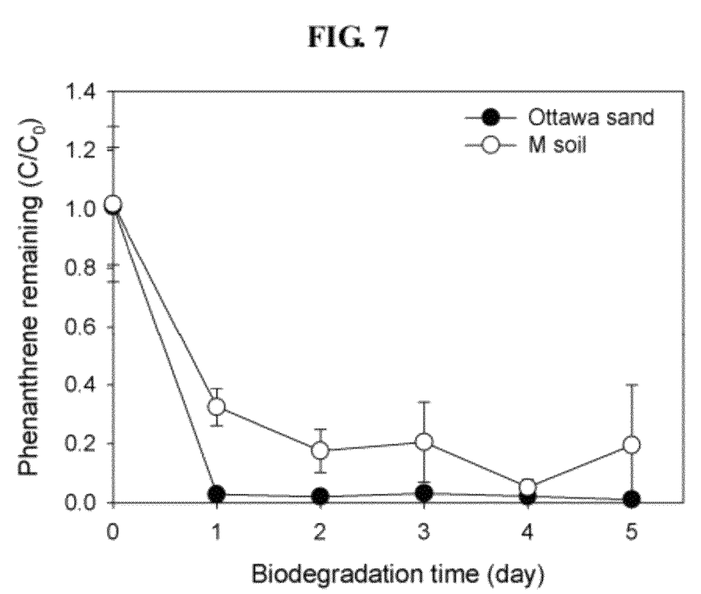
FIG. 7 is a graph illustrating a biodegradation by a recombinant strain with respect to phenanthrene of about 500 mg/kg per day in a model soil and a real soil.

FIG. 7 is a graph illustrating a biodegradation by a recombinant strain with respect to phenanthrene of about 500 mg/kg per day in a model soil and a real soil.

Referring to FIG. 7, the biodegradation of phenanthrene of about 500 mg/kg per day in the model soil and the biodegradation of phenanthrene of about 500 mg/kg per day in the real soil are 97.2% and 68.2%, respectively. When phenanthrene of about 500 mg/kg in the model soil is degraded based on the biodegradation of 97.2%, phenanthrene of about 486 mg/kg may remain. When phenanthrene of about 500 mg/kg in the real soil is degraded based on the decomposition efficiency of 68.2%, phenanthrene of about 341 mg/kg may remain. In this example, it is assumed that phenanthrene with phenanthrene concentrations of below about 500 mg/kg, for example, phenanthrene concentrations of about 50 mg/kg through about 250 mg/kg, is all degraded.

Figure 8:
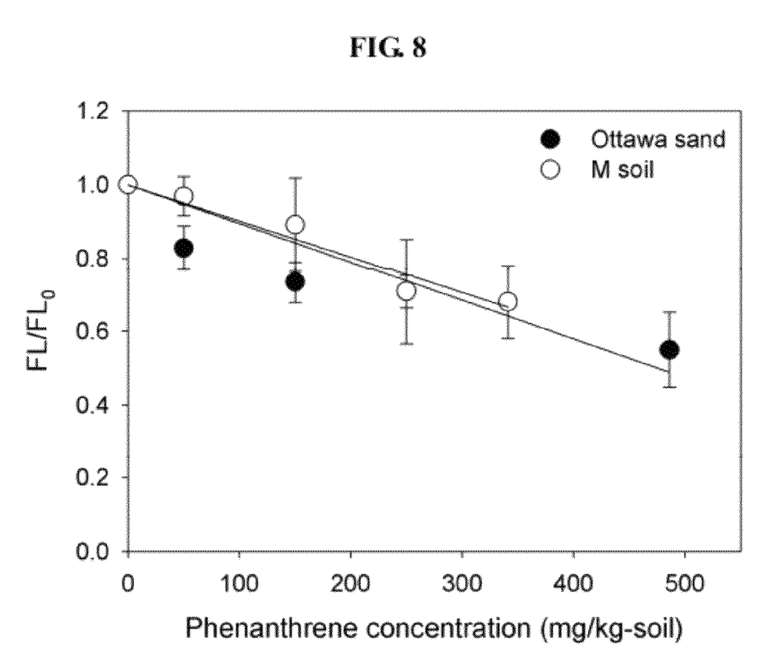
FIG. 8 is a graph comparing a reaction of a recombinant strain with respect to phenanthrene remaining in a model soil with a reaction of the recombinant strain with respect to phenanthrene remaining in a real soil, an amount of phenanthrene remaining in each of the model soil and the real soil being calculated based on a corresponding biodegradation.

FIG. 8 is a graph comparing a reaction of a recombinant strain with respect to phenanthrene remaining in a model soil with a reaction of the recombinant strain with respect to phenanthrene remaining in a real soil, an amount of phenanthrene remaining in each of the model soil and the real soil being calculated based on a corresponding biodegradation.

Referring to FIG. 8, a difference between the reaction of the recombinant strain measured in the model soil and the reaction of the recombinant strain measured in the real soil does not exist. Soil particles may not affect measuring of a fluorescence reaction of the recombinant strain and thus, the reaction of the recombinant strain may be measured based on an availability of phenanthrene. Therefore, an applicability of the recombinant strain with respect to the real soil is verified.

The recombinant strain adopts a new detection mechanism, and visualizes and quantifies a toxicity and a bioavailability of aromatic hydrocarbons and thus, may provide a digitalized microorganism-based system that visualizes and quantifies a state of oil contamination and a residual toxicity.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. An isolated *Sphingomonas paucimobilis* comprising SEQ ID NO. 1, being deposited with a deposition number KCTC 11771BP.

2. The isolated *Sphingomonas paucimobilis* of claim 1, wherein *Sphingomonas paucimobilis* cell death measures a contaminant included in soil or water sample, wherein the contaminant is an aromatic hydrocarbon.

3. The *Sphingomonas paucimobilis* of claim 2, wherein the aromatic hydrocarbon is phenanthrene.

4. A method of specifically measuring aromatic hydrocarbons as a contaminant in a sample using an isolated number of dead *Sphingomonas paucimobilis* of claim 1.

\* \* \* \* \*